US006224884B1

(12) United States Patent
Remy

(10) Patent No.: US 6,224,884 B1
(45) Date of Patent: *May 1, 2001

(54) PROCESS FOR THE PREPARATION OF PHOTOCHROMIC TITANIUM OXIDE, COMPOUND OBTAINED AND COMPOSITION COMPRISING IT

(75) Inventor: Christophe Remy, Thomery (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/139,279

(22) Filed: Aug. 25, 1998

(30) Foreign Application Priority Data

Aug. 26, 1997 (FR) .................................................. 97 10659

(51) Int. Cl.$^7$ ........................................................ A61K 7/48
(52) U.S. Cl. ................... 424/401; 423/611; 423/610; 424/400; 424/401; 424/59; 424/61; 424/63; 424/64; 424/70.1; 424/450; 424/489
(58) Field of Search ...................... 423/611, 612; 424/400, 401, 489, 61, 63, 64, 70.1, 45, 450, 59; 514/944, 945, 937, 938

(56) References Cited

U.S. PATENT DOCUMENTS

| 2,622,964 | * | 12/1952 | Aagaard et al. ........................ 23/202 |
| 3,903,239 | * | 9/1975 | Berkovich ............................... 423/82 |
| 4,724,138 | | 2/1988 | Duffy et al. . | |
| 5,024,827 | * | 6/1991 | Jones et al. ............................ 423/610 |
| 5,176,905 | | 1/1993 | Ohno et al. . | |
| 5,628,934 | * | 5/1997 | Ohno et al. ............................. 252/586 |
| 5,700,451 | * | 12/1997 | Yue et al. ................................. 424/59 |
| 5,846,511 | * | 12/1998 | Kim et al. ............................... 423/610 |

FOREIGN PATENT DOCUMENTS

| 4 302 896 | 8/1994 | (DE) . |
| 0 359 909 | 3/1990 | (EP) . |
| 0 526 712 | 2/1993 | (EP) . |
| 0 624 553 | 10/1994 | (EP) . |
| 1 604 929 | 6/1972 | (FR) . |
| 2 209 717 | 7/1974 | (FR) . |
| 5-17152 | 11/1991 | (JP) . |

OTHER PUBLICATIONS

Derwent Publications, Ltd., Japanese Patent Application No. 09030933, Section Ch, Week 9715.
R.W. Fitzpatrick et al., "Amorphous and Crystalline Titanium and Iron–Titanium Oxides in Synthetic Preparations, at Near Ambient Conditions, and in Soil Clays", Clay and Clay Minerals, vol. 26, No. 3, pp. 189–201, 1978.
English Language Derwent Abstract of DE 4 302 896.
English Language Derwent Abstract of FR 1 604 929.
English Language Derwent Abstract of FR 2 209 717.
English Language Derwent Abstract of JP 5–17152.

* cited by examiner

Primary Examiner—Thurman K. Page
Assistant Examiner—P. E. McQueeney
(74) Attorney, Agent, or Firm—Finnegan, Henderson, Farabow, Garrett & Dunner, L.L.P.

(57) ABSTRACT

A process for the preparation of a photochromic titanium oxide, by heat-treating a hydrolysed mixture of titanium chloride and a metal precursor; the titanium oxide photochromic compounds obtained; and compositions comprising the compounds.

43 Claims, No Drawings

PROCESS FOR THE PREPARATION OF PHOTOCHROMIC TITANIUM OXIDE, COMPOUND OBTAINED AND COMPOSITION COMPRISING IT

Applicant references herein the patent application of CHRISTOPHE REMY for USE OF AN IONIC CONDUCTOR IN ORDER TO IMPROVE PHOTOCHROMISM, AND COMPOSITION COMPRISING IT (09/139,280) filed on even date herewith and incorporates the disclosure thereof specifically by reference herein.

The present invention relates to the improvement of the photochromic properties of a titanium oxide, by virtue of a novel synthesis process; the invention also relates to the novel compound which is obtained, and to its application in the field of cosmetic compositions in particular.

Cosmetic compositions, in particular make-up compositions such as free or compact powders, foundations, blushers or eye-shadows, lipsticks or nail varnishes, include a suitable vehicle and various colorants intended to impart some degree of colour to the said compositions before and/or after they are applied to the skin, the mucous membranes, the mucocutaneous tissues and/or parts of the exoskeleton, for example the nails or the hair.

A fairly limited range of colorants is presently used to create colours, in particular lakes, inorganic pigments or pearlescent pigments. Lakes allow vivid colours to be obtained, but are for the most part unstable with respect to light, temperature or pH. Some of them also have the drawback of staining the skin unattractively after they have been applied, as a result of the colorant being leached. Conversely, inorganic pigments, in particular inorganic oxides, are highly stable but give somewhat dull and pale colours. In order to obtain coloured effects, use may also be made of pearlescent pigments whose colours are varied, albeit never intense, which make it possible to obtain iridescent but most often fairly weak effects.

It has therefore been proposed to use photochromic compounds in make-up or haircare compositions, so as to obtain attractive and varied changes in the colour effect of make-up for the skin and/or the hair.

Photochromic compounds are compounds which have the property of changing colour when they are exposed to a light source, then of returning to their initial colour, or a similar colour, when they are no longer being exposed. In particular, compounds of this type have a particularly advantageous application in cosmetic compositions, in particular in make-up compositions such as foundations and blushers or eye-shadows. Indeed, it has been found that the make-up effect of skin which has been made up differs depending on whether the illumination is natural or artificial. Thus, make-up applied under artificial illumination will appear lighter under natural light. Conversely, make-up applied out of doors will appear darker in a place where the illumination is artificial.

The photochromic properties of a compound can be characterized using trichromatic coordinates (L, a and b) in the way described before the examples. These coordinates make it possible, in particular, to determine a parameter $\Delta E$ which will be used in the present application to characterize the photochromism of the compounds according to the invention and outside the scope of the invention.

In general, the higher the parameter $\Delta E$ is, the more the compound is photochromic.

The prior art has, in particular, proposed the use in cosmetics of organic photochromic compounds, for example compounds of the spiropyran or naphthoxazine families.

These photochromic compounds are particularly advantageous since they enable the support to which they are applied to change colour rapidly when the said support is exposed to UV, for example, with a rapid return to the initial colour when it is no longer being exposed to UV.

Mention may thus be made of French Patent FR1604929, which describes cosmetic compositions, in particular for the hair, in aerosol form which contain phototropic compounds such as nitrobenzylpyridines, thiosemicarbazones or spiropyran derivatives. After these compositions have been sprayed onto the hair and exposed to sunlight, a blue-violet coloration is obtained which returns to pale yellow in darkness.

Cosmetic compositions comprising particular inorganic photochromic compounds, selected from metal oxides, their hydrated forms and their complexes, have also been proposed, for example by European Patent EP359909. In particular, this document mentions the use of titanium oxide, treated so as to make it photochromic, in make-up compositions such as powders and foundations.

Furthermore, document U.S. Pat. No. 5,176,905 discloses a process for obtaining a photochromic titanium oxide by mixing iron hydroxide (FeOOH) and titanium dioxide, and calcining at 750–850° C.

In addition, document EP624553 discloses a process for the preparation of titanium oxide having improved photochromism, involving dissolving an organotitanium and an organic compound comprising at least one metal, in an organic solvent, then in hydrolyzing the mixture, recovering the hydrolysate and calcining it at a temperature of 550–700° C. This gives a photochromic titanium oxide having a colour difference which can be quantified using the parameter $\Delta E$ whose value is at least equal to 10. The value $\Delta E$ is the measured difference between the chromaticity before exposure and the chromaticity after exposure for 1 hour, under UV at 2 mW/cm$^2$.

Also, document JP05/017152 discloses a process for the preparation of a photochromic titanium oxide, including mixing organotitaniums with at least one metal selected from iron, chromium, copper, nickel, vanadium or manganese, then in sintering the said mixture in the presence of sodium compounds. It is in this way possible to obtain a parameter $\Delta E$ which is improved in comparison with the prior art, and in particular greater than 10. The parameter $\Delta E$ is calculated in the same way as in EP624553.

Also, the article by Fitzpatrick et al., published in the journal "Clays and Clay Minerals" Volume 26, No. 3, pp. 189–201 (1978) discloses a process for the preparation of titanium and iron oxide coprecipitates by hydrolysis; the powder which is obtained can, in particular, be calcined, but only up to a temperature of 250° C.

However, it has been observed that the compounds obtained in this way do not have the desired photochromic properties.

There is still the need to provide photochromic compounds which make it possible to obtain strong photochromism, and in particular make it possible to obtain an appreciable change in the colour of the make-up, that is to say a relatively high $\Delta E$, in particular greater than or equal to 12.

An object of the present invention is to provide a particular process for the preparation of compounds of this type.

The present invention therefore relates to a process for the preparation of a photochromic titanium oxide, in which:
a mixture is prepared comprising titanium chloride and a precursor of a metal selected from iron, chromium, copper, nickel, manganese, cobalt and molybdenum, the mixture is hydrolysed, then the mixture obtained is heat-treated at a temperature of at least 300° C. so as to obtain a compound having a parameter ΔE greater than or equal to 12.

The invention also relates to the photochromic compound of the titanium oxide type which can be obtained by the above process, as well as to a composition, in particular a cosmetic composition, comprising the compound.

The process according to the invention therefore involves heat-treating a mixture comprising a titanium chloride and at least one precursor of a metal.

The titanium chloride may, in particular, be $TiCl_4$.

The term "precursor of a metal" is intended to mean any compound comprising the said metal and capable of releasing it.

Use may, in particular, be made of a hydrate, an oxide and a salt, such as a sulphate or a chloride, of the said metal. The metal is preferably selected from iron, chromium, copper, nickel, manganese, cobalt and molybdenum, alone or as a mixture.

Use is preferably made of an iron chloride or sulphate.

Preferably, use is made of a metal precursor in liquid form or in pulverulent form.

Generally, the amounts of the compounds are selected so as to obtain a "metal oxide equivalent":"titanium oxide equivalent" ratio preferably ranging from 0.05:100 to 10:100, more preferably from 0.1:100 to 2:100.

The mixture which is obtained is then hydrolysed by adding a Brönsted base, preferably a strong base such as ammonia solution, or more easily using water or a slightly basic aqueous solution.

This treatment makes it possible to hydrolyse the titanium chloride and convert it into "titanium gel" (a name given by analogy with silicone gels).

The hydrolysis may, in particular, be carried out at ambient temperature, ranging from 20 to 30° C. The hydrolysis is carried out until a mixture preferably having a pH of 2 to 10, in particular 5 to 6 is obtained.

The mixture may then be heat-pretreated preferably at 70–110° C., more preferably at 80–100° C., for 2–10 hours, more preferably 4–7 hours. An at least partially amorphous titanium oxide which does not have adequate photochromic properties is then obtained.

The titanium oxide is generally in the form of a powder in suspension in the reaction medium; the said powder may be filtered, washed and dried by the usual means.

The resulting compound is then heat-treated at a temperature preferably of at least 300° C., more preferably at a temperature preferably ranging from 400 to 800° C., and still more preferably from 500 to 700° C., for enough time to calcine the compound, that is to say to obtain an at least partially crystalline titanium oxide which will have the desired photochromic properties.

The temperature should not, however, be such that it permits conversion of the titanium in the anatase form into titanium in rutile form. This is because it is important to keep the anatase crystallographic form for the titanium oxide, since the "rutile" form does not lead to adequate photochromism.

The heat-treatment time may preferably be 2 to 8 hours, more preferably 3 to 5 hours, and depends in particular on the calcining temperature.

The person skilled in the art will know how to adjust the calcining "temperature/time" pairing according to the desired result, on the basis of his general knowledge.

Titanium oxides having good photochromic properties are obtained in this way. In particular, the parameter ΔE of the compounds according to the invention is preferably at least greater than or equal to 12, in particular greater than or equal to 15, 20 or even 25.

The photochromic compound treated according to the process of the invention may be incorporated in a composition, in particular a cosmetic composition, in an amount which can be readily determined by the person skilled in the art, on the basis of his general knowledge, and which may preferably range from 0.01 to 30% by weight relative to the total weight of the composition, more preferably in an amount ranging from 1 to 15% by weight.

The cosmetic composition may be in the form of a product to be applied to the mucous membranes, the mucocutaneous tissues and/or the keratinous tissues, such as the skin and parts of the exoskeleton (nails, eyelashes, eyebrows, body hair and head hair). It therefore contains a cosmetically acceptable medium, that is to say a medium which is compatible with all the keratinous materials such as the skin, the nails, the hair, the eyelashes and eyebrows, the mucous membranes and the mucocutaneous tissues, and any other cutaneous region of the body and the face. The said medium may comprise or be in the form of, in particular, a suspension, a dispersion, a solution in solvent or aqueous-alcoholic medium, optionally thickened or gelled; an oil-in-water, water-in-oil or multiple emulsion; a gel or a foam; an emulsified gel; a dispersion of vesicles, in particular lipid vesicles; a two-phase or multi-phase lotion; a spray; a free, compact or loose powder; an anhydrous paste. The person skilled in the art will be able to select the suitable pharmaceutical form, as well as the method of preparing it, on the basis of his general knowledge, while taking into account both the nature of the constituents which are used, in particular their solubility in the support, and the application envisaged for the composition.

When the composition is in aqueous form, in particular in the form of a dispersion, emulsion or aqueous solution, it may comprise an aqueous phase which may comprise water, a floral water such as cornflower water, and/or a mineral water such as l'eau de Vittel, les eaux du bassin de Vichy, l'eau d'Uriage, l'eau de la Roche Posay, l'eau de la Bourboule, l'eau d'Enghien-les-Bains, l'eau de Saint Gervais-les-Bains, l'eau de Néris-les-Bains, l'eau d'Allevar-les-Bains, l'eau de Digne, l'eau de Lucas, l'eau de Maizières, l'eau de Neyrac-les-Bains, l'eau de Lons-le-Saunier, les Eaux Bonnes, l'eau de Rochefort, l'eau de Saint Christau, l'eau des Fumades and l'eau de Tercis-les-bains.

The aqueous phase may comprise from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

When the composition according to the invention is in the form of an emulsion, it may optionally furthermore comprise a surfactant, preferably in an amount of 0.01 to 30% by weight relative to the total weight of the composition.

Among the anionic surfactants which may be used, alone or as a mixture, mention may in particular be made of alkali metal salts, ammonium salts, amine salts or amino alcohol salts of the following compounds: alkyl sulphates, alkyl ether sulphates, alkylamide sulphates and ether sulphates, alkylarylpolyether sulphates, monoglyceride sulphates, alkylsulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkylsulphosuccinamates, alkyl sulphoacetates, alkyl polyglycerol carboxylates, alkyl phosphates/alkyl ether phosphates, acyl sarcosinates, alkylpolypeptidates, alkylamidopolypeptidates, acyl isethionates, and alkyl laurates. The alkyl or acyl radical in all of these compounds generally denotes a chain of 12 to 18 carbon atoms. Mention may also be made of soaps and fatty acid salts such as oleic acid, ricinoleic acid, palmitic acid, stearic acid, coconut oil acid or hydrogenated coconut oil acid and, in particular, amine salts such as amine stearates; acyl lactylates in which the acyl radical comprises 8–20 carbon atoms; carboxylic acids of polyglycol ethers corresponding to the formula: Alk-(OCH$_2$—CH$_2$)$_n$—OCH$_2$—COOH in acid or salified form, in which the substituent Alk corresponds to a straight chain having 12 to 18 carbon atoms and in which n is an integer ranging from 5 to 15.

Among the non-ionic surfactants which may be used, alone or as a mixture, mention may in particular be made of: polyethoxylated, polypropoxylated or polyglycerolated fatty acids, alkylphenols and alcohols which have a fatty chain containing 8 to 18 carbon atoms; copolymers of ethylene oxide and of propylene oxide, condensates of ethylene oxide and of propylene oxide with fatty alcohols, polyethoxylated fatty amides, polyethoxylated fatty amines, ethanolamides, fatty acid esters of glycol, fatty acid esters of oxyethylenated or non-oxyethylenated sorbitan, fatty acid esters of saccharose, fatty acid esters of polyethylene glycol, phosphoric triesters, fatty acid esters of glucose derivatives; alkyl polyglycosides and alkylamides of amino sugars; condensation products of an α-diol, of a monoalcohol, of an alkylphenol, of an amide or a diglycolamide with glycidol or a glycidol precursor.

The composition according to the invention may also comprise 0 to 5% by weight, relative to the total weight of the emulsion, of at least one co-emulsifier which may be selected from oxyethylenated sorbitan monostearate, fatty alcohols such as stearyl alcohol or cetyl alcohol, or fatty acid esters of polyols such as glyceryl stearate.

The composition according to the invention may furthermore comprise one or more thickeners in preferred concentrations ranging from 0 to 6% by weight, relative to the total weight of the composition, selected from:

polysaccharide biopolymers such as xanthan gum, carob gum, guar gum, alginates, modified celluloses such as hydroxyethylcellulose, methylcellulose, hydroxypropylcellulose and carboxymethylcellulose, starch derivatives, cellulose ether derivatives containing quaternary ammonium groups, and cationic polysaccharides;

synthetic polymers, for instance polyacrylic acids such as polyglyceryl (meth)acrylate polymers such as Hispagel or Lubragel from the companies Hispano Quimica or Gardian, polyvinylpyrrolidone, polyvinyl alcohol, crosslinked polymers of acrylamide and of ammonium acrylate such as PAS 5161 or Bozepol C from Hoechst; acrylate/octylacrylamide copolymers such as Dermacryl from National Starch; polyacrylamide-based polymers such as Sepigel 305 from Seppic, crosslinked polymers of acrylamide and of methacryloyloxyethyl-trimethylammonium chloride such as Salcare SC 92 from Allied Colloids, magnesium aluminium silicate.

Depending on the application envisaged, the composition may furthermore comprise a film-forming polymer. This is, in particular, the case when it is desired to prepare a composition of the nail varnish, mascara or eye-liner type or a haircare composition of the lacquer type. The polymers may be dissolved or dispersed in the cosmetically acceptable medium. In particular, the polymer may be present in the form of a solution in an organic solvent or in the form of an aqueous dispersion of film-forming polymer particles. The said polymer may be selected from nitrocellulose, cellulose acetobutyrate, polyvinyl butyrals, alkyd resins, polyesters, acrylics, vinyls and/or polyurethanes. Mention may, in particular, be made of the copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl (meth)acrylate and/or isobutyl (meth)acrylate/C$_1$–C$_4$ alkyl (meth)acrylate copolymers; (meth)acrylic acid/ethyl acrylate/methyl methacrylate terpolymers and tetrapolymers; methyl methacrylate/butyl or ethyl acrylate/hydroxyethyl or 2-hydroxypropyl acrylate or methacrylate/(meth)acrylic acid tetrapolymers; copolymers of acrylic acid and of C$_1$–C$_4$ alkyl methacrylate; terpolymers of vinylpyrrolidone, of acrylic acid and of C$_{1-20}$ methacrylate; amphoteric copolymers; vinyl esters of branched acids; vinyl esters of benzoic acid; copolymers of (meth)acrylic acid and of at least one olefinic monomer; copolymers of vinyl monoacid and/or of allylic monoacid. Among the resins, mention may be made of resins of the arylsulphonamide formaldehyde or arylsulphonamide epoxy type; resins of the acrylic, styrene, styreneacrylate and vinylacrylate type.

The composition may also comprise at least one plasticizer, such as tricresyl phosphate, benzyl benzoate, triethyl citrate, tributyl citrate, triethyl acetyl citrate, 2-triethylhexyl acetyl citrate, camphor; glycol ethers; castor oil oxyethylenated with 40 mol of ethylene oxide; propylene glycol; butyl glycol; ethylene glycol monomethyl ether acetate; propylene glycol ethers; ester ethers of propylene glycol and ethylene glycol; esters of diacids such as diethyl, dibutyl and diisopropyl phthalates and adipates, diethyl and dibutyl tartrates, diethyl and dibutyl succinates, diethyl and dibutyl sebacates, diethyl, dibutyl and 2-diethylhexyl phosphates, diethyl or dibutyl acetyl citrate; glyceryl esters. The plasticizers may generally be present at a level ranging from 1% to 40% by weight relative to the total weight of the composition.

The composition according to the invention may also comprise a fatty phase, in particular comprising fatty substances which are liquid at 25° C., such as oils of animal, vegetable, mineral or synthetic origin; fatty substances which are solid at 25° C., such as waxes of animal, vegetable, mineral or synthetic origin; fatty substances in paste form; gums; mixtures thereof.

The compositions according to the invention may thus comprise volatile oils, which evaporate on contact with the skin but whose presence in the cosmetic composition is useful since they make it easier to spread the composition when it is applied to the skin. Spreading agents of this type, referred to here as "volatile oils" are generally oils which, at 25° C., have a saturated vapour pressure at least equal to 0.5 millibar (i.e. 50 Pa). Use is preferably made of oils whose flashpoint is high enough to allow these oils to be used in formulation, and low enough to obtain the desired evanescent effect. Oils whose flashpoint is of the order of 40–100° C. are preferably employed.

Mention may thus be made of volatile silicone oils, such as:

cyclic volatile silicones having 3 to 8, and preferably 4 to 6, silicon atoms. Examples of these include cyclotetradimethylsiloxane, cyclopentadimethylsiloxane or cyclohexadimethylsiloxane, cyclocopolymers of the dimethylsiloxane/methylalkylsiloxane type, such as Silicone FZ 3109 marketed by the company Union Carbide, which is a dimethylsiloxane/methyloctylsiloxane cyclocopolymer, linear volatile silicones having 2 to 9 silicon atoms. Examples of these include hexamethyldisiloxane, hexylheptamethyltrisiloxane or octylheptamethyltrisiloxane.

Mention may also be made of volatile hydrocarbon oils such as isoparaffins and, in particular, isododecane; and fluorinated oils such as the one marketed under the name GALDEN® (Montefluos).

Use may also be made of non-volatile oils, among which mention may be made of:

poly($C_1$–$C_{20}$)alkylsiloxanes and, in particular, those having trimethylsilyl end groups, preferably those whose viscosity is less than 0.06 $m^2$/s, among which mention may be made of linear polydimethylsiloxanes and alkylmethylpolysiloxanes such as cetyldimethicone (CTFA name), silicones modified with aliphatic and/or aromatic groups, which may or may not contain fluorine, or with functional groups such as hydroxyl, thiol, and/or amine groups, phenylated silicone oils, in particular those of formula:

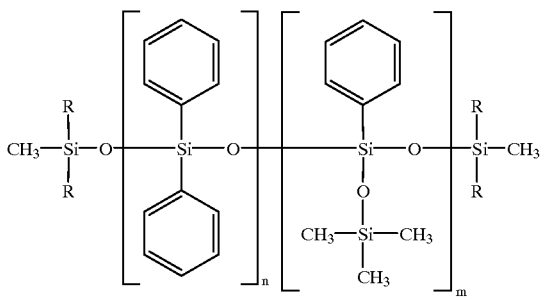

in which R is a $C_1$–$C_{30}$ alkyl radical, an aryl radical or an aralkyl radical, n is an integer ranging from 0 to 100, and m is an integer ranging from 0 to 100, with the condition that the sum of m+n ranges from 1 to 100, oils of animal, vegetable or mineral origin, and in particular animal or vegetable oils formed by fatty acid esters of polyols, in particular liquid triglycerides, for example sunflower oil, corn oil, soybean oil, marrow oil, grapeseed oil, sesame oil, hazelnut oil, apricot oil, almond oil or avocado oil; fish oils, glyceryl tricaprocaprylate, or vegetable or animal oils of formula $R_1COOR_2$ in which $R_1$ represents a higher fatty acid residue containing from 7 to 19 carbon atoms and $R_2$ represents a branched hydrocarbon chain containing 3 to 20 carbon atoms, for example Purcellin oil; liquid paraffin, liquid petroleum jelly, perhydrosqualene, wheatgerm oil, beauty-leaf oil, sesame oil, macadamia oil, grapeseed oil, colza oil, copra oil, groundnut oil, palm oil, castor oil, jojoba oil, olive oil or cereal germ oil; fatty acid esters; alcohols; acetylglycerides; octanoates, decanoates or ricinoleates of alcohols or of polyalcohols; fatty acid triglycerides; glycerides;

fluorinated and perfluorinated oils.

The composition according to the invention may furthermore comprise other fatty substances, which may be selected by the person skilled in the art on the basis of his general knowledge, so as to give the final composition the desired properties, for example in terms of consistency and/or texture. These additional fatty substances may be waxes, gums and/or fatty substances in paste form or of animal, vegetable, mineral or synthetic origin, as well as mixtures thereof.

Mention may, in particular, be made of:

silicone gums, waxes of animal, vegetable, mineral or synthetic origin, such as microcrystalline waxes, paraffin, petrolatum, petroleum jelly, ozokerite, montan wax; beeswax, lanolin and derivatives thereof; candelilla wax, ouricury wax, carnauba wax, japan wax, cocoa butter, cork fibre wax or sugarcane wax; hydrogenated oils which are solid at 25° C., ozokerites, fatty esters and glycerides which are solid at 25° C.; polyethylene waxes and waxes obtained by Fischer-Tropsch synthesis; hydrogenated oils which are solid at 25° C.; lanolins; fatty esters which are solid at 25° C.; silicone waxes; fluorinated waxes.

The composition according to the invention may also comprise one or more organic solvents which are cosmetically acceptable (acceptable in terms of tolerance, toxicology and feel). These organic solvents may preferably represent 0% to 98% of the total weight of the composition and may be selected from hydrophilic organic solvents, lipophilic organic solvents, amphiphilic solvents or mixtures thereof.

Among the hydrophilic organic solvents, mention may, for example, be made of linear or branched lower monoalcohols having 1 to 8 carbon atoms, such as ethanol, propanol, butanol, isopropanol, isobutanol; polyethylene glycols having 6 to 80 ethylene oxides; polyols such as propylene glycol, isoprene glycol, butylene glycol, glycerol and sorbitol; mono- or dialkyl isosorbide in which the alkyl groups have 1 to 5 carbon atoms; glycol ethers such as diethylene glycol monomethyl or monoethyl ether and propylene glycol ethers such as dipropylene glycol methyl ether. As amphiphilic organic solvents, mention may be made of polyols such as polypropylene glycol (PPG) derivatives such as fatty acid esters of polypropylene glycol and fatty alcohol esters of PPG, for example PPG-23 oleyl ether and PPG-36 oleate. As lipophilic organic solvents, mention may, for example, be made of fatty esters such as diisopropyl adipate, dioctyl adipate, alkylbenzoates, isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, bis(2-hexylethyl)succinate, diisostearyl malate, 2-octyldodecyl lactate, glyceryl triisostearate and diglyceryl triisostearate.

The composition may furthermore comprise a particulate phase, which may comprise pigments and/or pearlescent agents and/or fillers customarily used in cosmetic compositions. The term pigments should be understood to mean white or coloured, inorganic or organic particles intended to colour and/or opacify the composition. The term fillers should be understood to mean colourless or white, inorganic or synthetic, lamellar or non-lamellar particles intended to give the composition body or rigidity, and/or softness, a matt effect and uniformity when applied as make-up. The term pearlescent agents should be understood to mean iridescent particles which reflect light.

The pigments may be present in the composition preferably at a level of up to 15% by weight of the final composition, and more preferably at a level of 8 to 10% by weight. They may be white or coloured, inorganic and/or organic, and of customary or nanometric size. Mention may be made of the dioxides of titanium, zirconium or cerium, as well as the oxides of zinc, iron or chromium, ferric blue, chromium hydrate, carbon black, ultramarines (aluminosilicate polysulphides), manganese pyrophosphate and certain metal powders such as those of silver or of aluminium, and carbon black. Mention may also be made of the lakes commonly used to give a make-up effect to the lips and the skin, these lakes being salts of calcium, barium, aluminium or zirconium and acidic colorants.

The pearlescent agents may be present in the composition at a level preferably of up to 20% by weight, more preferably in a proportion of the order of 8 to 15% by weight. Examples of the pearlescent agents which may be envisaged include natural mother-of-pearl, mica coated with titanium oxide, with iron oxide, with natural pigment or with bismuth oxychloride, as well as coloured titanium mica.

The fillers, which may be present at a level preferably of up to 30% by weight, more preferably 5 to 15%, in the composition, may be inorganic or synthetic, lamellar or non-lamellar. Mention may be made of talc, mica, silica, kaolin, nylon powders and polyethylene powders, TEFLON, starch, boron nitride, polymer microspheres such as EXPANCEL (Nobel Industrie), polytrap (Dow Corning) and of silicone resin microbeads (TOSPEARLS from Toshiba for example), precipitated calcium carbonate, magnesium carbonate or hydrocarbonate, metal soaps derived from organic carboxylic acids having 8 to 22 carbon atoms.

Depending on the type of formulation, the pulverulent phase may represent 0.01 to 99% by weight of the composition.

The composition may furthermore comprise a colorant, in particular a natural organic colorant such as cochineal carmine, and/or a synthetic colorant such as halo acid, azo or anthraquinone dyes. Mention may also be made of inorganic colorants such as copper sulphate.

The composition may furthermore comprise any additive customarily used in the field of cosmetics, for example antioxidants, fragrances, essential oils, preserving agents, lipophilic or hydrophilic cosmetic active agents, moisturizers, vitamins, essential fatty acids, sphingolipids, self-tanning agents such as DHA, sunscreens, anti-foaming agents, sequestering agents and antioxidants.

Naturally, the person skilled in the art will take care to select the optional additional compounds, and/or their amount, so that the advantageous properties of the composition according to the invention are not, or not substantially, adversely affected by the addition which is envisaged.

The cosmetic compositions may be in the form of a care and/or make-up product for the skin, a suncare or self-tanning product or even a haircare product. In particular, they are particularly applied in the field of lipsticks, foundations, blushers or eye-shadows, free or compact powders, tinted creams, eye-liners, mascaras and solvent or aqueous nail varnishes.

The invention is illustrated in more detail in the following examples, which are in no way limiting.

Method of Determining the Parameter $\Delta E$ Using Trichromatic Coordinates

The powdered compound is packed in a metal dish.

The trichromatic coordinates (L0, a0, b0) of the packed powder are measured using a Minolta CR300 colorimeter.

The dish is exposed for 30 minutes using a 365 nm UV lamp, then the new coordinates (L30, a30 and b30) are measured which reflect the colour change due to the exposure.

The parameter $\Delta E$ is defined in the following way; this parameter is characteristic of the photochromic activity of the compound; the higher this parameter is, the more photochromic the material will be.

$$\Delta E=[(L30-L0)^2+(a30-a0)^2+(b30-b0)^2]^{1/2}$$

EXAMPLE 1

A mixture comprising 15 ml of titanium chloride ($TiCl_4$) and 0.22 g of iron chloride ($FeCl_3$) in aqueous solution at 41% by weight was prepared.

A 10% strength ammonia solution was added dropwise while stirring, until a pH of 5.5 was obtained.

The mixture was heated under reflux at 90° C. for 5 hours, then stirring was continued at room temperature for 24 hours. The mixture was filtered, and the filtrate was washed and dried at 55° C. for 24 hours.

A powder was obtained which was calcined for 4 hours at 600° C.

Iron-doped titanium oxide was obtained.

EXAMPLE 2

Various processes for synthesizing iron-doped photochromic titanium oxide were carried out in order to compare photochromic properties of the compounds obtained.

For each synthesis method, a study was carried out in order to find the experimental parameters which give the best properties.

The following table indicates the maximum value of $\Delta E$ obtained for each synthesis method, which a priori indicates the optimum photochromic properties which can be obtained with each synthesis method.

| Synthesis method | $\Delta E$ |
|---|---|
| A | 10 |
| B | 9 |
| C | 9 |
| D | 15 |
| E | 12 |
| F (invention) | 22 |

A: calcining titanium oxide and iron chloride ($FeCl_3$) at 900° C. for 4 hours
B: aqueous dispersion of titanium oxide and iron chloride, neutralization with NaOH, filtration and calcining at 800° C. for 4 hours.
C: aqueous dispersion of titanium oxide and iron chloride, neutralization with NaOH, addition of urea, filtration and calcining at 800° C. for 4 hours.
D: synthesis from titanium oxysulphate (see EP526712)
E: synthesis from titanium alkoxide (see EP624553)
F: Example 1

It is therefore seen that the process according to the invention does indeed make it possible to obtain a photochromic titanium oxide having properties which are improved in comparison with the prior art.

EXAMPLE 3

The preparation process according to Example 1 was repeated while varying the calcining temperature, with the other parameters remaining unchanged.

The following results are obtained.:

| Temperature | ΔE |
|---|---|
| 300° C. | 6 |
| 400° C. | 23 |
| 600° C. | 29 |
| 800° C. | 2 |

It is therefore seen that the choice of calcining temperature is important for obtaining good photochromic properties.

EXAMPLE 4

The preparation process according to Example 1 was repeated while varying the amount of iron present in the titanium oxide, with the other parameters remaining unchanged.

The following results are obtained:

| Iron % (by weight) | ΔE |
|---|---|
| 0.1% | 6 |
| 0.4% | 29 |
| 0.8% | 15 |
| 1.0% | 14 |

EXAMPLE 5

| A compacted powder having the following composition was prepared: | |
|---|---|
| talc | 30 g |
| mica | 20 g |
| nylon powder | 16 g |
| zinc stearate | 5 g |
| iron oxide | 2 g |
| titanium oxide according to Example 1 | 10 g |
| fatty binder | qs 100 g |
| A composition having good cosmetic properties were obtained. | |

I claim:

1. A process for preparing a titanium oxide photochromic compound comprising:
   preparing a mixture comprising titanium chloride and an effective amount of at least one precursor of a metal, wherein said titanium chloride is $TiCl_4$,
   hydrolysing said mixture at an ambient temperature, and
   heat-treating said mixture under conditions sufficient to obtain a titanium oxide photochromic compound having a parameter ΔE of at least 12.

2. A process according to claim 1, wherein said sufficient conditions include a temperature of at least 300° C.

3. A process according to claim 2, wherein said metal is selected from iron, chromium, copper, nickel, manganese, cobalt and molybdenum.

4. A process according to claim 1, wherein said parameter ΔE is at least 15.

5. A process according to claim 4, wherein said parameter, ΔE is at least 20.

6. A process according to claim 5, wherein said parameter ΔE is at least 25.

7. A process according claim 1, wherein said at least one precursor is selected from hydrates, oxides and salts of said metal.

8. A process according to claim 7, wherein said salts are selected from sulphates and chlorides.

9. A process according to claim 7, wherein said at least one precursor of a metal is iron chloride or iron sulphate.

10. A process according to claim 9, wherein said at least one precursor of a metal is in liquid or pulverulent form.

11. A process according to claim 1, wherein said titanium chloride and said metal precursor are present in an amount such that the ratio of "metal oxide equivalent":"titanium oxide equivalent" ranges from 0.05:100 to 10:100.

12. A process according to claim 11, wherein said ratio ranges from 0.1:100 to 2:100.

13. A process according to claim 1, wherein said hydrolysing is carried out by adding a Brönsted base or using water or a slightly basic aqueous solution.

14. A process according to claim 13, wherein said Brönsted base is a strong base.

15. A process according to claim 13, wherein said Brönsted base is an ammonia solution.

16. A process according to claim 1, wherein said hydrolysing is carried at a temperature ranging from 20 to 30° C.

17. A process according to claim 16, wherein after hydrolysing, said mixture has a pH ranging from 2 to 10.

18. A process according to claim 17, wherein after hydrolysing, said mixture has a pH ranging from 5 to 6.

19. A process according to claim 1, wherein between said hydrolysing step and said heat-treating step, said mixture is heat-pretreated from 2 to 10 hours at 70 to 110° C.

20. A process according to claim 19, wherein said mixture is heat-pretreated from 4 to 7 hours at 80 to 100° C.

21. A process according to claim 1, wherein said heat treating is carried out at a temperature ranging from 400 to 800° C.

22. A process according to claim 21, wherein said heat treating is carried out at a temperature ranging from 500 to 700° C.

23. A process according to claim 1, wherein said heat-treating lasts for a time sufficient to calcine said titanium oxide photochromic compound, but the titanium does not convert from the anatase form to the rutile form.

24. A process according to claim 23, wherein said heat-treating lasts from 2 to 8 hours.

25. A process according to claim 24, wherein said heat-treating lasts from 3 to 5 hours.

26. A titanium oxide photochromic compound with a parameter ΔE of at least 12 obtained by a process according to claim 1.

27. A titanium oxide photochromic compound according to claim 26, wherein said parameter ΔE is at least 15.

28. A titanium oxide photochromic compound according to claim 27, wherein said parameter ΔE is at least 20.

29. A titanium oxide photochromic compound according to claim 28, wherein said parameter ΔE is at least 25.

30. A cosmetic composition comprising a titanium oxide photochromic compound with a parameter ΔE of at least 12 obtained by a process according to claim 1.

31. A composition according to claim 30, wherein said at least one titanium oxide photochromic compound is present in an amount ranging from 0.01 to 30% by weight relative to the total weight of said cosmetic composition.

32. A composition according to claim 31, wherein said at least one titanium oxide photochromic compound is present in an amount ranging from 1 to 15% by weight relative to the total weight of said cosmetic composition.

33. A composition according to claim 30, wherein said composition is to be applied to mucous membranes, mucocutaneous tissues, and/or keratinous tissues.

34. A composition according to claim 30, wherein said composition further includes a cosmetically acceptable medium.

35. A composition according to claim 34, wherein said cosmetically acceptable medium is in the form of a suspension, a dispersion, a solution in solvent or aqueous-alcoholic medium; an oil-in-water, water-in-oil or multiple emulsion; a gel or foam; an emulsified gel; a dispersion of vesicles; a two-phase or multi-phase lotion; a spray; a free, compact or loose powder; or an anhydrous paste.

36. A composition according to claim 35, wherein said suspension, dispersion or solution is thickened or gelled.

37. A composition according to claim 35, wherein said vesicles are lipid vesicles.

38. A composition according to claim 30, wherein said composition further includes an aqueous phase.

39. A composition according to claim 38, wherein said aqueous phase comprises up to 14% by weight, relative to the total weight of said aqueous phase, of a $C_2$–$C_6$ lower monoalcohol and/or a polyol.

40. A composition according to claim 39, wherein said polyol is selected from glycerol, butylene glycol, isoprene glycol, propylene glycol and polyethylene glycol.

41. A composition according to claim 30, wherein said composition is in the form of a care and/or make-up product for the skin, a suncare or self-tanning product, or a haircare product.

42. A composition according to claim 30, wherein said composition is in the form of a lip composition, a foundation, a blusher or eye-shadow, a free or compact powder, a tinted cream, an eye-liner, a mascara or a nail varnish.

43. A process according to claim 1, wherein said heat-treating is carried out at a temperature ranging from 300 to 700° C.

* * * * *